(12) United States Patent
Niazi

(10) Patent No.: US 9,499,290 B2
(45) Date of Patent: Nov. 22, 2016

(54) STATIONARY BUBBLE REACTORS

(75) Inventor: Sarfaraz K. Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 127 days.

(21) Appl. No.: 13/194,970

(22) Filed: Jul. 31, 2011

(65) Prior Publication Data

US 2011/0287404 A1 Nov. 24, 2011

Related U.S. Application Data

(63) Continuation of application No. 12/719,836, filed on Mar. 8, 2010.

(51) Int. Cl.
| | | |
|---|---|---|
| *B65B 63/08* | (2006.01) | |
| *B01F 15/00* | (2006.01) | |
| *C12M 1/00* | (2006.01) | |
| *C07K 14/00* | (2006.01) | |
| *C12M 1/36* | (2006.01) | |
| *C12N 1/00* | (2006.01) | |
| *C12N 1/16* | (2006.01) | |
| *C12N 1/20* | (2006.01) | |
| *C12N 5/04* | (2006.01) | |
| *B01F 3/04* | (2006.01) | |

(52) U.S. Cl.
CPC ........... *B65B 63/08* (2013.01); *B01F 15/0085* (2013.01); *C07K 14/00* (2013.01); *C12M 1/36* (2013.01); *C12M 23/14* (2013.01); *C12N 1/00* (2013.01); *C12N 1/16* (2013.01); *C12N 1/20* (2013.01); *C12N 5/04* (2013.01); *B01F 3/04269* (2013.01); *B01F 2003/04148* (2013.01); *B01F 2003/04312* (2013.01)

(58) Field of Classification Search
CPC .................... C12M 23/14; B01F 2003/04148; B01F 2003/04312; B01F 3/04269
USPC ...................................................... 435/289.1
See application file for complete search history.

(56) References Cited

U.S. PATENT DOCUMENTS

| | | | | |
|---|---|---|---|---|
| 2,871,820 A | * | 2/1959 | Hayden .......................... | 119/261 |
| 4,029,581 A | * | 6/1977 | Clough et al. ................ | 210/220 |
| 5,071,760 A | * | 12/1991 | Watanabe et al. ............ | 435/394 |
| 5,858,283 A | * | 1/1999 | Burris ................. | B01F 3/04269 |
| | | | | 156/290 |
| 6,063,618 A | * | 5/2000 | Weuster-Botz et al. ... | 435/294.1 |
| 6,237,898 B1 | | 5/2001 | Lafont | |
| 6,432,698 B1 | * | 8/2002 | Gaugler ................. | C12M 23/14 |
| | | | | 435/296.1 |
| 2009/0215155 A1 | * | 8/2009 | Cloud et al. ................ | 435/257.1 |
| 2010/0015696 A1 | * | 1/2010 | Claes et al. ................ | 435/303.3 |

* cited by examiner

Primary Examiner — Jonathan Hurst
(74) Attorney, Agent, or Firm — Therapeutic Proteins International, LLC; Sarfaraz K. Niazi

(57) ABSTRACT

Reactors that allow mixing and gasification by converting the entire floor of the reactor vessel to a sparge filter is described.

11 Claims, 4 Drawing Sheets

STATIONARY BUBBLE REACTORS

INTRODUCTION

Reactors are used for a variety of physical, chemical and biological processing. More commonly, these include mixing and gasification of liquid.

Liquid mixing is a major unit process in many industries including bioprocessing, chemical, and pharmaceutical manufacturing. The common methods of mixing a liquid (or a mixture of liquids and solids) in a container include use of an impeller, rocking or shaking the vessel, sparging gases to move liquid, ultrasonic waves and several combinations of these methods.

Whereas, many of these mixing systems provide adequate quality of mixing as desired by the process, mixing of liquid in large containers, particularly the flexible disposable containers, remains a major problem. There is an unmet need to devise systems that would consume least amount of energy, produce lowest on the contents mixed, achieve mixing in the shortest period of time and produce consistent mixing results. Since mixing is a often an ancillary step in many other processes such a bioreaction, chemical reaction and manufacture of products, an efficient mixing system would yield highly profitable and time-saving operations in many industries.

Gasification is a process of adding a specific gas to a liquid; more commonly this includes adding gases like oxygen to grow biological organisms and tissues or using an inert gas to remove other gases like oxygen. A large number of applications from sewage treatment to bioprocessing of therapeutic proteins to operation of aquariums are dependent on gasification of liquids.

In most hard-walled containers, gases are introduced by a sparger, a device with plurality of pores that diffuse gases inside a liquid medium. A large variety of spargers are used, from the slow bubbling fish aquarium type to high-speed single point nozzles for the aeration of bioreactors. The efficiency of sparger is measured in the KLA value or liquid-air transport coefficient that describes how fast a gas saturation is reached. For example, at room temperature (25 C) the solubility of oxygen in water is about 8%; this decreases to about 6.5% at 37 C, the temperature most often used for bioprocessing. How fast is this maximum concentration of oxygen is reached in water upon starting gasification is a function of rate of gasification and mixing; also critical is the size of the bubble and thus the surface area of gas exposed to water. It is almost impossible to predict the KLA values since so many factors impact this value.

There remains an unmet need to develop a sparging system that would allow a uniform and quick dispersion of gases throughout the liquid, reducing dependence on mixing to achieve a uniform concentration.

There remains even a greater unmet need to develop reactor systems wherein both of these processes, mixing and gasification, are combined, reducing cost, work time while increasing the efficiency of the functionality of reactors.

BRIEF DESCRIPTION OF THE INVENTION

Gaseous bubbles have often been used in various industrial operations; for example, slug bubble bioreactors produce a large bubble that rises from the bottom of a vessel, pushing the culture media upwards as the bubble moves up and is discharged at the surface. Sparger of several types are installed at different locations inside a vessel to force air or other gases to force the movement of liquid inside the vessel.

U.S. Pat. No. 6,237,898 describes a bubble elevator that includes an orifice intermediate between the air tapping point for entraining liquid and the top opening for ejecting the air/liquid mixture.

U.S. Pat. No. 7,600,741 describes a gas bubble generator suitable for use in anaerobic digestion systems for treating waste sludge. The gas bubble generator is submerged within a large body of liquid and is attached to a stack pipe.

U.S. Pat. No. 7,374,675 describes a system and method of aerobic wastewater treatment that provides large mixing bubbles along with small oxygenating bubbles supplied by diffusers. The mixing bubbles are large enough to move wastewater and generate a mixing current as they rise to the surface.

The above represent just a few examples of how various devices including spargers and diffusers are used for the aeration of liquids while also making it possible to mix the liquids in a vessel. While many of these systems are suitable for smaller operations, mixing becomes a serious challenge in larger vessels where pockets of unmixed liquids may accumulate, particularly in vessels that are horizontally laid out like the flexible bags. Generally, a solution is found in increasing the gasification rate and intense mixing that whips up the liquids, requires very high energy, often causes degradation of the product and in those cases where a biological organism or cell is involved, results in reduced productivity.

The unmet need of a universal mixing system is addressed in the instant invention wherein a gas sparging system is installed at the bottom of a mixing vessel such that the entire bottom of the vessel acts as a sparger; this allows liquid to move upwards throughout the vessel providing adequate mixing. To achieve this goal, several design parameters become crucial.

For example, it is necessary that the gas be pushed as fine bubbles throughout the bottom surface and rising vertically to the top of the liquid surface. The intent is to keep the fluid movement as laminar as possible but at the same time add enough turbulence as well to assure optimal mixing. The size of air bubbles and the requirement that they break the top surface of the liquid at all points is important. One way to achieve this is to provide a sparging filter creating fine bubbles at the entire bottom surface of the container allowing these bubbles to rise upward to create both a laminar and turbulent mixing. This can be achieved by installing sparging filters of size and dimension to fit the entire surface of the bottom of the container. The filter can be made of various materials like ceramic, plastic, metal or any other such hard material. In most instances this would represent a filter with an inner volume and a port attached to the cavity or the inner volume through which a gas is introduced inside the filter.

Another method is to install a perforated false bottom in as a means of introducing a gas in the cavity between the false bottom and the real bottom. Since the false bottom has perforations, gas would escape through its perforations forming an upward stream that would push the liquid up and stir the liquid as bubbles move up, coalescing and forming larger bubbles and thus creating a turbulent mixing. As bubble size increases, it causes the liquid to be pushed around resulting in the interruption of the laminar flow and the Reynold number increases to provide a turbulent mixing.

Another critical design feature is that the perforations are of same size throughout the surface of the false bottom creating an imbalance of air flow, with higher flow rates nearer to the source of air input (because of higher pressure), moving the liquid more rapidly in the inside core if the source of gas is in the center) compared to other parts of the vessel where the flow rate is lower because the perforations are farther away from the source of gas introduced and thus push smaller volume of gas. This creates a differential movement of liquid in various parts of the vessel creating a cascade effect that can further enhance the mixing operations. It is important to realize that a critical component of this invention is to provide sufficient gas flow so that air bubbles break the top surface of the liquid at all point.

The false bottom can be made of the same material as the vessel such as a stainless steel material in large stainless steel bioreactors or it can be an additional layer of polyethylene in two-dimensional flexible disposable bags. If the false bottom is made of a pliable material such as polyethylene film, addition of gas behind the film would inevitably cause the false bottom to blow up and produce a convex surface inside the container; this is not desirable as it would change the gasification path and result in less than optimal mixing. To prevent this, the false bottom layer is attached to the real bottom layer by sealing the two layers at various points producing a tufting effect.

The gas inlet is placed preferably as central to the horizontal surface of the vessel to provide a uniform distribution of gas pressure behind the false bottom or the sparging filter. In those instances where the surface area is large such in large reactors, it may be necessary to introduce gas at various points along the horizontal surface to avoid larger pressure drops across the horizontal surface. In the absence of this modification, the pressure of gas used would have to be very large to make sure that gas breaks the horizontal top surface of the liquid.

The pores in the false bottom layer or the sparging filter need to be of a dimension such that air is not lost instantly as large bubbles to the container and for this purpose, the size of perforations is best kept at below 100 micron range; the size of pores determines the flow rate and thus results in pressure drop; larger pore sizes would cause the gas to escape without forming a pattern of flow. The optimal pore size would depend to a great extent on the viscosity of the liquid, the height of gas travel and the volume of liquid, all those parameters that determine the breakthrough pressure needed to push the gas inside the vessel as well as cause it to break the top surface of the liquid as well.

BRIEF DESCRIPTION OF DRAWINGS

FIG. 1 shows a typical example of a hard-walled container (1) used for mixing a liquid (10) that has a topical horizontal surface (11). The sparging filter (8) is a disc-shaped hard-walled device placed or affixed to the bottom of the container and has plurality pores (12) through which compressed gas (7) is discharged in an upward movement; the sparging filter is supplied with compressed gas with a tube (3) located centrally in the sparging filter. The container additionally contains a port for the exhaust of gas (9), a port for inlet and outlet of liquid (4), a port for drainage (5) and a stopcock (6) to control the drainage.

Figure 1:
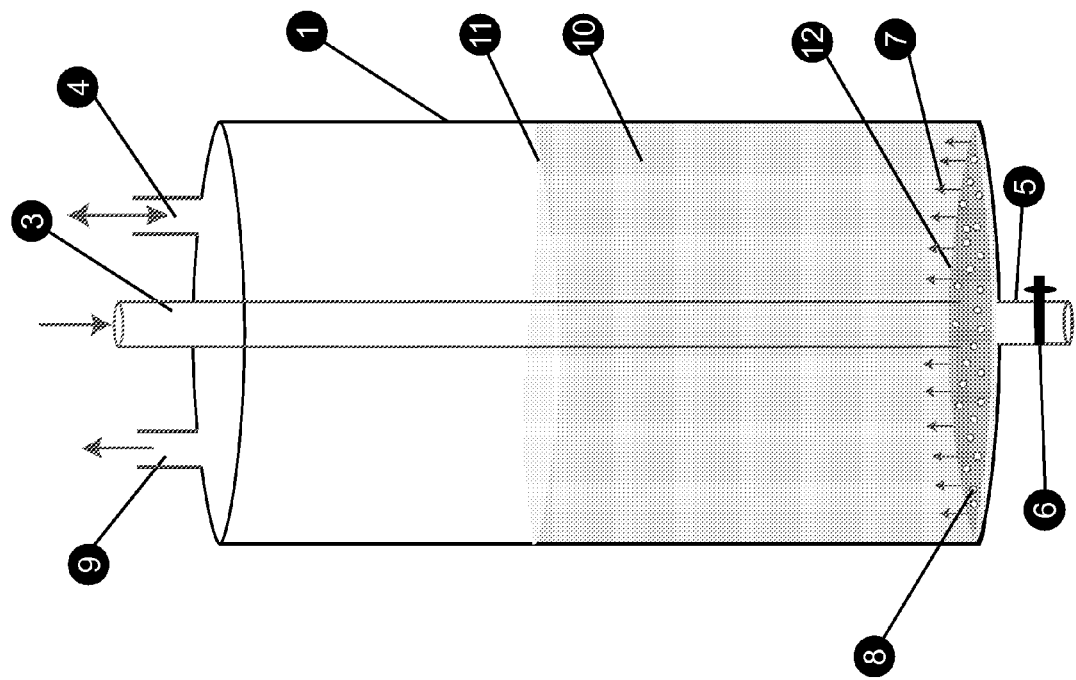
FIG. 1. Side view of a hard-walled cylindrical container with a sparging filter covering the entire bottom of the container.

The apparatus shown in FIG. 1 is operated by starting flow of gas that begins to flow out of the pores in the sparging filter and moves upwards pushing the liquid. The flow rate of the gas is maintained such that the entire upper surface of the liquid (11) begins to show bubbles breaking through it as an indication that the entire liquid is under motion further assuring that there will be no dead volumes anywhere in the container. The process is continued until a desired mixing property is obtained.

Figure 2:
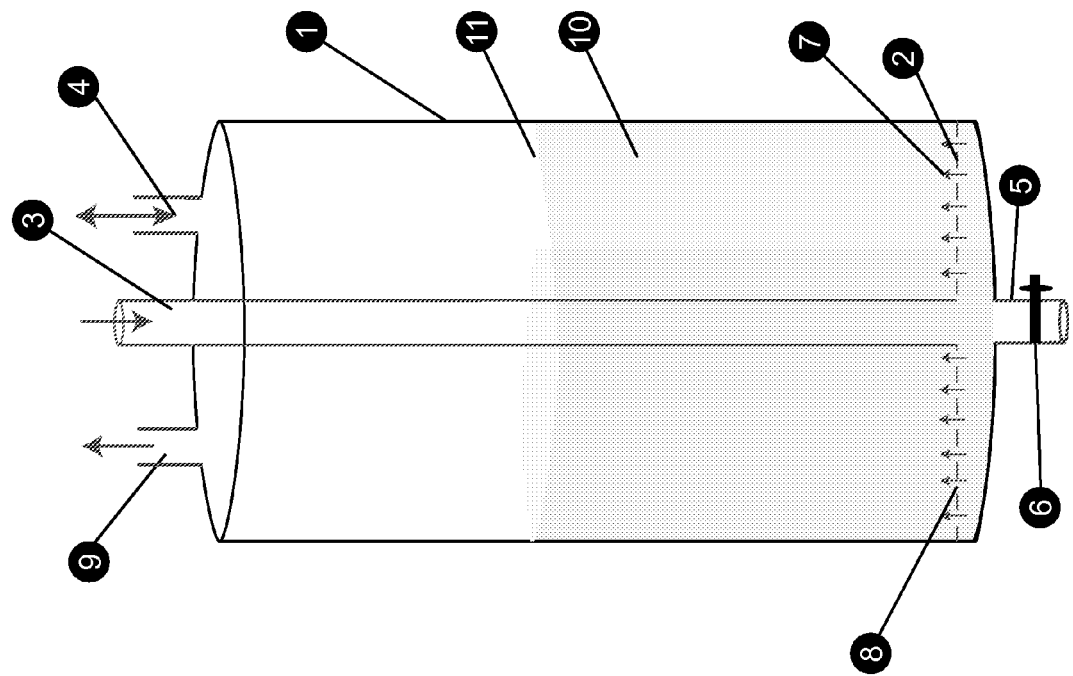

FIG. 2 shows a typical example of a hard-walled container (1) with a hard false bottom (8) serving as sparging filter used for mixing a liquid (10) that has a top horizontal surface (11). The sparging filter (8) is located at the bottom of the container and has plurality of pores (2) through which compressed gas is discharged (7) in an upward movement; the sparging filter is supplied with compressed gas with a tube (3) located centrally in the sparging filter. The container additionally contains a port for the exhaust of gas (9), a port for inlet and outlet of liquid (4), a port for drainage (5) and a stopcock (6) to control the drainage.

The apparatus shown in FIG. 2 is operated by starting flow of gas that begins to flow out of the pores in the sparging filter and moves upwards pushing the liquid. The flow rate of the gas is maintained such that the entire upper surface of the liquid begins to show bubbles breaking through it as an indication that the entire liquid is under motion assuring that there will be no dead volumes anywhere in the container. The process is continued until a desired mixing property is obtained.

Figure 3:
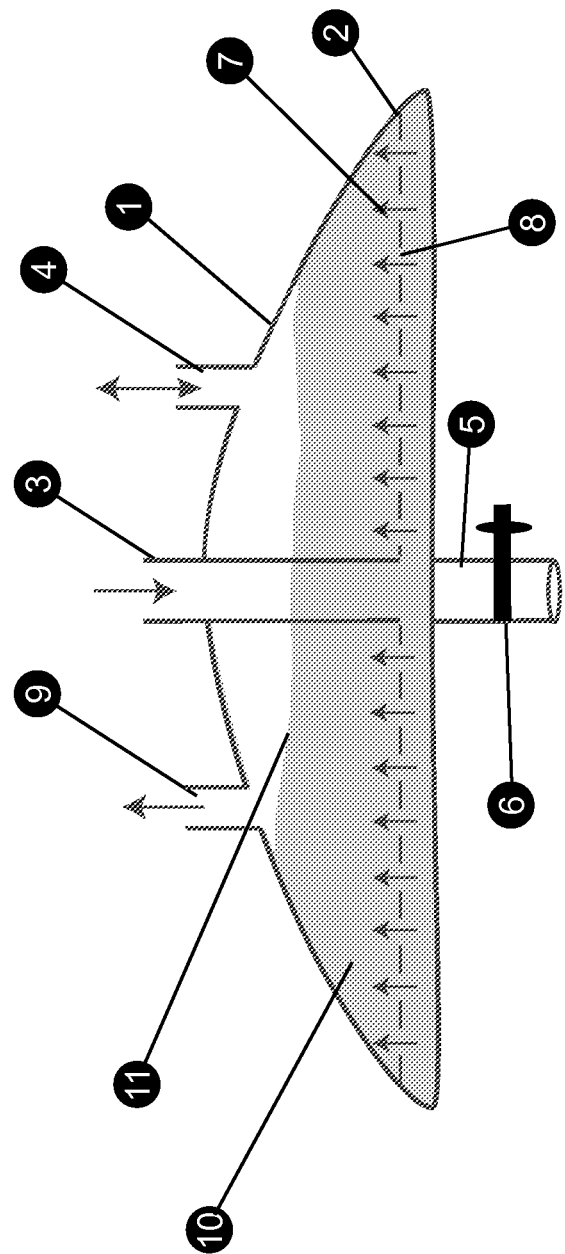

FIG. 3 shows a flexible container (1) with a flexible false bottom (2) acting as a sparging filter that has plurality of pores (8) that cause air to flow upwards (7); the container additionally has air exhaust port (9), air inlet port (3) and liquid inlet-outlet port (4); the container is capable of holding liquid (10) and has a topical horizontal surface (11) and has drain port (5) and a stopcock to control the drain (6).

The apparatus according to FIG. 3 is operated by a similar method to the one described for the apparatus shown in FIGS. 1 and 2.

Figure 4:
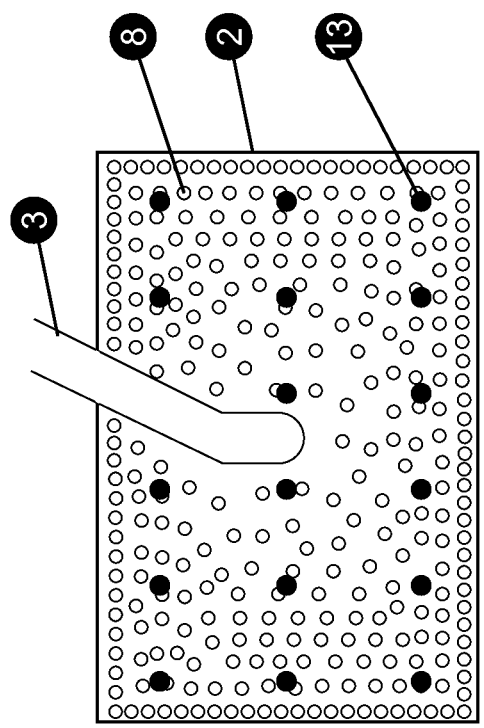

FIG. 4 shows a topical view of the sparging filter in FIGS. 1-3; the dimensions of the filter (2) match the dimension of the container bottom, it has a gas supply port (3), plurality of pores (8) and optionally tufting or sealing (13) of the filter to the bottom of container when the filter is pliable to keep it from bloating under the pressure of gas. Since the gas pressure is likely to be higher near the inlet point, this figure shows that the number of pores near the inlet point is reduced.

DETAILED DESCRIPTION OF THE INVENTION

The instant invention addresses two critical problems in a variety of industries where liquids are mixed or gasified. Historically, an impeller device that rotates fast inside a liquid volume creates a circular movement to mix liquids. Since the energy transfer to liquids is highly efficient, this remains as the most widely used method. The goal of impellers is to create a large enough circle of movement that would cause the movement of entire liquid; in some designs larger size impellers achieve it or smaller size impellers achieve it by high velocity.

A good example of this is found in the movement of boats. Large ships have impellers that move at a very slow speed but displace a very large volume of liquid while the onboard motors on smaller boats have a very small fan that rotates at a very high speed. In liquid mixing, often the containers have baffles to break the laminar movement of liquid generated by the circular motion of the impeller to increase the mixing efficiency.

In the bioprocessing industry, a bioreactor or a fermenter is a good example of a container that is in need of a good mixing system. For hard-walled containers used as bioreactors or fermenters, the obvious choice is to install impellers to generate movement of liquid and these are operated at a very high speed, 400-500 rpm, most often to achieve the mixing efficiency required.

However, it is widely known in the science and the art of growing biological organisms and cells that these grow better when allowed to stay in colonies or aggregates; the most frequently used method of mixing by using impellers destroys the aggregates and breaks the colonies resulting in a less than optimal growth yield. A more desirable solution would be to provide as laminar a mixing possible to reduce the shear on the living cells and organisms while assuring homogeneity of the liquid throughout its volume. This can be readily achieved as taught in the instant invention.

First, a sparging filter is chosen such that when placed at the bottom of the container, it covers the entire base of the container. This filter can be a disc-shaped ceramic device or a stainless steel device that has pores on both sides or only on one side (if the filter has pores on both sides, these can be blocked on one side by coating the filter with a resin). There is a gas inlet attached to the filter such that the inlet is as central to the filter as possible. For cylindrical vessels, this would not be difficult but for all other shaped there would inevitably be a misbalance as the longer edge of a rectangular shape would be closer to the gasification inlet than the shorter edge. In all instances, the pressure of gas near to the gas entry point will be higher resulting in faster flow through the pores nearest to the inlet; to circumvent this, the density of pores near to the inlet point can be reduced, either by design (e.g., when creating a perforated false bottom or blocking some pores nearer to the gas inlet).

This configuration is shown in FIG. 4. While this feature of variable density of pores is described as an element of invention, it is not required since the behavior of liquid would depend to a great degree on several other factors which include liquid density, viscosity, height of liquid column, temperature of liquid, the volume of liquid, the dimensions of the container, the pressure and flow of gas, the type of sparging filter used, etc., the factor of variable density of pores would impact but to an uncertain degree.

In some instances, having a uniform density of pores may be beneficial, as it would result in a stratification of the columns of liquids rising above with the center column having the fastest velocity. This would create a cascade effect, like a fountain with a major spout in the center, to produce efficient mixing.

More specifically, the instant invention can be used to mix the contents of a liquid contained in a flexible or hard-walled container. Once liquids or solid and liquid mixtures are placed inside a container containing the instant invention installed, the airflow is commenced that causes the liquid to move up and then down causing mixing.

The instant invention produces both vertical and horizontal mixing; as the air bubbles rise, they coalesce and produce a compression force of variable dimension producing lateral flow of liquid. The time taken to achieve a homogenous mixing would depend to a great degree on the density, viscosity, temperature, gas flow rate and the dimension and geometry of the container. All of these parameters can be readily validated by a single mixing validation study that would require adding a dye to the liquid and studying its distribution and concentration over time; based on these data, each of the vessel types and the liquid mixed in it routinely are validated.

Some of the examples of mixing types that would greatly benefit from the instant invention include operations of bioreactors, media and buffer mixing in the bioprocess industry and in preparation of solutions in the manufacturing such as pharmaceutical manufacturing and in hundreds and thousands of other such application in just about every industry where the composition of liquid is a critical parameter in manufacturing operations.

Another application of the instant invention is in gasification of liquids, a unit process most commonly used in the bioprocess industry, sewer treatment, organ and blood tissue maintenance, aquariums and thousands of other applications. Since the entire bottom of the vessel acts as a sparging filter, it is relatively easy to provide maximum gasification of the liquid in the container; for the purpose of calculations of the efficiency of gasification, constants like KLA are widely used; even though these calculations are of lesser value in some situations, nevertheless, it is expected that the instant invention would provide the highest possible KLA values of any comparable system.

For more specific applications, the two uses described above can be combined in a bioreactor to provide optimal conditions for the growth of cells and organisms in culture media. This would then constitute a stationary bioreactor of the lowest cost and of the highest efficiency possible. Thousands of applications of these types of bioreactors are possible, from the wine industry to recombinant drug production.

What is claimed is:

1. A flexible horizontally disposed disposable bioreactor bag capable of holding nutrient media comprising:
   a flexible top sheet, a porous flexible middle sheet, and a flexible bottom sheet, the porous flexible middle sheet tufted to the flexible bottom sheet to form a sparging compartment covering essentially an entire bottom surface of the bioreactor bag, wherein the flexible top sheet and the flexible bottom sheet are sealed together at their edges and the sparging compartment serves to aerate and mix nutrient media located in a nutrient media compartment formed between the flexible top sheet and the porous flexible middle sheet;
   a gas inlet that extends through the nutrient media compartment to the sparging compartment to an inlet point near a central location of the flexible middle sheet to provide compressed gas to the sparging compartment;
   at least one nutrient media inlet port in fluid communication with the nutrient media compartment; and
   at least one compressed gas outlet port in fluid communication with the nutrient media compartment,
   wherein the porous flexible middle sheet allows the compressed gas from the gas inlet to aerate the nutrient media compartment from the sparging compartment, and
   wherein a plurality of pores of the flexible middle sheet are arranged so that pores located proximal to the inlet point near the central location of the flexible middle sheet are less densely dispersed than pores located proximal to an outer edge of the flexible middle sheet.

2. A disposable bioreactor bag comprising:
   a) a flexible top sheet;
   b) a flexible bottom sheet sealed together with the flexible top sheet at their edges;
   c) a porous flexible middle sheet tufted to the flexible bottom sheet to form (i) a sparging compartment between the porous flexible middle sheet and the flexible bottom sheet, the sparging compartment covering essentially an entire bottom surface of the bag, and (ii) a nutrient media compartment between the porous flexible middle sheet and the flexible top sheet;
   d) a gas inlet that extends through the nutrient media compartment to the sparging compartment to an inlet point near a central location of the flexible middle sheet to provide compressed gas to the sparging compartment;
e) at least one nutrient media inlet port in fluid communication with the nutrient media compartment; and
f) at least one compressed gas outlet port in fluid communication with the nutrient media compartment,
wherein the porous middle sheet allows the compressed gas from the gas inlet to aerate the nutrient media compartment from the sparging compartment, and
wherein a plurality of pores of the flexible middle sheet are arranged so that pores located proximal to the inlet point near the central location of the flexible middle sheet are less densely dispersed than pores located proximal to an outer edge of the flexible middle sheet.

3. The bioreactor of claim 1 or claim 2, wherein said plurality of pores each has a diameter less than 100 μm in size.

4. The bioreactor of claim 1 or claim 2, wherein said plurality of pores each has a diameter less than 10 pm in size.

5. The bioreactor of claim 1, wherein the flexible bottom sheet includes a liquid drain port directly connected to the sparging compartment.

6. The bioreactor of claim 1, wherein the gas inlet extends through the flexible top sheet to a center of the porous flexible middle sheet to provide compressed gas to the sparging compartment.

7. The bioreactor of claim 1, wherein the porous flexible middle sheet is tufted to the flexible bottom sheet at a plurality of locations.

8. The bioreactor of claim 1 or claim 2, wherein the middle sheet produces horizontal and vertical mixing.

9. The bioreactor of claim 2, wherein the flexible bottom sheet includes a liquid drain port directly connected to the sparging compartment.

10. The bioreactor of claim 2, wherein the gas inlet extends through the flexible top sheet to a center of the porous flexible middle sheet to provide compressed gas to the sparging compartment.

11. The bioreactor of claim 2, wherein the porous flexible middle sheet is tufted to the flexible bottom sheet at a plurality of locations.

* * * * *